United States Patent [19]

Kopp et al.

[11] Patent Number: 4,680,367

[45] Date of Patent: Jul. 14, 1987

[54] PROCESS FOR THE PRODUCTION OF UREA GROUP-CONTAINING POLYISOCYANATES

[75] Inventors: Richard Kopp, Cologne; Gerhard Grögler, Leverkusen; Heinrich Hess, Leverkusen; Klaus König, Leverkusen, all of Fed. Rep. of Germany

[73] Assignee: Bayer Aktiengesellschaft, Leverkusen, Fed. Rep. of Germany

[21] Appl. No.: 783,590

[22] Filed: Oct. 3, 1985

[30] Foreign Application Priority Data

Oct. 20, 1984 [DE] Fed. Rep. of Germany ....... 3438527

[51] Int. Cl.$^4$ .................. C08G 18/00; C08G 18/08
[52] U.S. Cl. ............................. 528/44; 528/48
[58] Field of Search .................................. 528/44

[56] References Cited

U.S. PATENT DOCUMENTS

| | | | |
|---|---|---|---|
| 2,597,025 | 5/1952 | Orth | 528/52 |
| 2,757,184 | 7/1956 | Pelley | 560/336 |
| 2,757,185 | 7/1956 | Barthel | 528/44 |
| 2,818,404 | 12/1957 | Hill | 528/44 |
| 2,902,474 | 9/1959 | Arnold et al. | 528/44 |
| 3,428,592 | 2/1969 | Yonker | 528/44 |
| 3,906,019 | 9/1975 | Campbell et al. | 560/352 |
| 4,032,516 | 6/1977 | McGarr | 260/77.5 A |
| 4,049,632 | 9/1977 | Magnusson et al. | 528/44 |
| 4,293,679 | 10/1981 | Cogliano | 528/48 |
| 4,403,083 | 9/1983 | Marans et al. | 528/44 |

*Primary Examiner*—John Kight
*Assistant Examiner*—Dennis R. Daley
*Attorney, Agent, or Firm*—Gene Harsh; Joseph C. Gil; Thomas W. Roy

[57] ABSTRACT

The present invention is directed to a process for the production of urea group-containing, finely divided solid polyisocyanates by emulsifying or suspending a urea group-free organic polyisoycanate in an excess of water so that said organic polyisocyanate amounts to about 1 to 65% by weight of the reaction mixture, said water containing about 0.01 to 5% by weight, based on the aqueous phase, of a protective colloid and reacting the organic polyisocyanate with water to yeild a urea group-containing polyisocyanate.

9 Claims, No Drawings

PROCESS FOR THE PRODUCTION OF UREA GROUP-CONTAINING POLYISOCYANATES

BACKGROUND OF THE INVENTION

1. Field of the Invention

This invention relates to a process for the production of finely divided, urea group-containing solid polyisocyanates by reacting urea group-free organic polyisocyanates with water, the organic polyisocyanate initially being converted in a large excess of water (based on the quantity of polyisocyanate) according to the invention in the presence of a protective colloid and optionally an emulsifier, to a stable emulsion or suspension and the reaction of the polyisocyanate with water optionally being carried out by addition of catalysts and/or bases, to produce urea group-containing polyisocyanates.

2. Description of the Prior Art

Processes for the production of urea group-containing polyisocyanates are known in the prior art. The production of reactive resin compositions by reacting an aromatic diisocyanate with from 0.1 to 0.9 mol of water per mol of diisocyanate in a solvent, which is capable of dissolving both the water and the diisocyanate and which shows a basic reaction in the presence of water, for example pyridine, is described for example in U.S. Pat. No. 2,597,025. The resin compositions are stable in storage with the exclusion of moisture and harden in the presence of atmospheric moisture within a very short time to produce an infusible, insoluble material, presumably a polyurea. The urea group-containing polyisocyanates dissolved in the reaction medium are not isolated. The production and isolation of urea group-containing polyisocyanates of defined composition is not an object.

U.S. Pat. No. 2,757,184 describes the production of substituted di(isocyanatophenyl)-ureas by reacting about 1 mol of water with 2 mol of diisocyanate in inert solvents containing oxygen atoms in the molecule, such as ethers, esters and ketones. In some solvents of this group, for example diethylethers or more preferably diisopropylethers (see DE-Applicattion No. P 3,419,429, Example 4) products are obtained which correspond practically in their NCO-content to the theoretical value. This production process, however, suffers from the disadvantage that organic solvents must be used, which pose considerable safety problems due to their volatility and oxidation tendency (ethers) and thus give rise to high processing costs. The products produced in these solvents, which occur in the form of small needle shaped crystals, likewise have a tendency to agglomerate during the work-up (filtration), so that an expensive grinding process is subsequently necessary, if a finely-divided product is to be obtained. If the product is ground, for example, in an air jet mill, a very finely-divided powder is obtained which has a very low bulk density (about 0.10–0.15 g/cm$^3$) and thus demands a large storage volume.

U.S. Pat. No. 3,906,019 describes the production of di(isocyanatotolyl)ureas, wherein one of the reaction constituents, water or toluylene-diisocyanate, is added in excess and acts as the reaction medium. The resulting di(isocyanatotolyl)ureas are insoluble in both reaction constituents and immediately crystallize out after their formation. The reaction between water and diisocyanate is catalyzed by addition of compounds of the Lewis-base-type or the Lewis-acid-type. Water is preferably added in stoichiometric excess and then acts as reaction medium.

From 5 to 15 parts of water are preferably added to from 20 to 40 parts of diisocyanate. The products have an NCO-content, which is reduced by about $\geq 10$ rel % in comparison to the theoretical NCO-content. 60, 83 and 65% by weight of urea diisocyanate are given as the yield of the three described examples. If the examples, in which water is used in excess, are adjusted (column 3, lines 1–16; column 3, line 45; column 4, line 7) several important disadvantages of this process can be established.

1. The reaction between the diisocyanate and the water takes place very exothermically with the given water and catalyst quantities; the reaction temperature in the described small-scale mixture on this page, lines 8–20, can only be maintained under 40° C. by cooling with ice sodium chloride bath as described. This fact is likely to lead to great difficulties, particularly in largescale technical usage, since a considerable quantity of $CO_2$ is released within a short time.

2. The resulting urea diisocyanate agglomerates immediately and precipitates on the wall of the reaction vessel in the form of a thick, hard layer. After reaction, this can only be removed from the reaction container with difficulty, for example by cooling the reaction vessel including the product to $-60°$ C., whereby the product which has become brittle and fragile can then be removed from the wall of the container in great chunks. After drying, a grinding process is necessary in all cases.

3. The pyridine, preferably used as a catalyst during reaction, is not completely removed by the work-up described in the patent (washing with hexane or ethyl acetate). An extremely unpleasant and aggravating pyridine odor thereby clings to the products, which can also cause problems during further use of the products through evaporation and uncontrollable catalysis.

4. The yields are all under 85%, so that ecological problems occur during the removal of the separated liquid phase.

The production process described in U.S. Pat. No. 3,906,019, which is limited to toluylene-diisocyanate, in which an excess of water is used for the first time as reaction medium suffers in the disclosed form from substantial disadvantages. An object of the present invention was to develop a process for the production of solid urea group-containing polyisocyanates in water as the reaction medium, in which these disadvantages no longer arise. It was attempted, in particular, to produce the polyisocyanate particles in as large a yield as possible and in such a finely-divided form, that the products can be worked-up problem-free and a subsequent grinding process becomes unnecessary for most uses.

SUMMARY OF THE INVENTION

The present invention is directed to a process for the production of urea group-containing, finely divided solid polyisocyanates by emulsifying or suspending a urea group-free organic polyisocyanate in an excess of water so that said organic polyisocyanate amounts to about 1 to 65% by weight of the reaction mixture, said water containing about 0.01 to 5% by weight, based on the aqueous phase, of a protective colloid and reacting the organic polyisocyanate with water to yield a urea group-containing polyisocyanate.

DETAILED DESCRIPTION OF THE INVENTION

The initial dispersion of the polyisocyanate in the aqueous phase is facilitated by suitable emulsifying or dispersing agents.

When carrying out the process according to the invention, aliphatic, cycloaliphatic, araliphatic, aromatic and heterocyclic polyisocyanates are used as urea group-free starting polyisocyanates, as described, for example, by W. Siefken in Justus Liebigs Annalen der Chemie, 562, pages 75 to 136, for example those of the formula $$Q(NCO)_n$$

wherein, n is from 2 to 4, preferably 2, and

Q represents an aliphatic hydrocarbon radical having 2 to 18, preferably 6 to 10 carbon atoms, a cycloaliphatic hydrocarbon radical having 4 to 15, preferably 5 to 10 carbon atoms, an aromatic hydrocarbon radical having 6 to 15, preferably 6 to 13 carbon atoms, or an araliphatic hydrocarbon radical having 8 to 15, preferably 8 to 13 carbon atoms. Examples include ethylenediisocyanate, 1,4-tetramethylene-diisocyanate, 1,6-hexamethylene diisocyanate, 1,12-dodecane-diisocyanate, cyclobutane-1,3-diisocyanate, cyclohexane-1,3- and -1,4-diisocyanate as well as desired mixtures of the stereo-isomers, 1-isocyanato-3,3,5-trimethyl-5-isocyanatomethyl-cyclohexane (DE-published application No. 1,202,785, U.S. Pat. No. 3,401,190), 2,4- and 2,6-hexahydrotoluylene-diisocyanate as well as desired mixtures of these isomers, hexahydro-1,3- and/or -1,4-phenylenediisocyanate, perhydro-2,4'- and/or -4,4'-diphenylmethane-diisocyanate, 1,3- and 1,4-phenylene-diisocyanate, 2,4- and 2,6-toluylene-diisocyanate as well as desired mixtures of these isomers, diphenylmethane-2,4'-and/or -4,4'- and/or -2,2'-diisocyanate and naphthylene-1,5-diisocyanate.

Furthermore, the following are also suitable according to the invention: triphenylmethane-4,4',4"triisocyanate; polyphenyl-polymethylene-polyisocyanates obtained by aniline-formaldehyde-condensation and subsequent phosgenation and described, for example, in G.B. Patent No. 874,430 and 848,671; m- and p-isocyanatophenyl-sulphonyl-isocyanates according to U.S. Pat. No. 3,454,606; perchloric arylpolyisocyanates as described, for example, in DE-published application 1,157,601 (U.S. Pat. No. 3,277,138); polyisocyanates having carbodiimide groups as described in DE Patent No. 1,092,007 (U.S. Pat. No. 3,152,162) as well as in DE-laid open applications Nos. 2,504,400, 2,537,685 and 2,552,350; norbornane-diisocyanates according to U.S. Pat. No. 3,492,330; polyisocyanates having allophanate-groups as described, for example, in G.B. Patent No. 994,890, BE Patent No. 761,626 and NL Patent application No. 7,102,524; polyisocyanates having isocyanurate groups described, for example, in U.S. Pat. No. 3,001,973, DE Patent Nos. 1,022,789, 1,222,067 and 1,027,394 as well as in DE-laid open applications Nos. 1,929,034 and 2,004,048; polyisocyanates having urethane groups as described, for example, in BE Patent No. 752,261 or in U.S. Pat. Nos. 3,394,164 and 3,644,457; polyisocyanates according to DE Patent No. 1,230,778 having acylated urea groups; polyisocyanates having biuret groups as described, for example, in U.S. Pat. Nos. 3,124,605, 3,201,372 and 3,124,605 as well as in G.B. Patent No. 889,050; polyisocyanates produced by telomerization reactions as described, for example, in U.S. Pat. No. 3,654,106; polyisocyanates having ester groups as described, for example, in G.B. Patents Nos. 965,474 and 1,072,956, in U.S. Pat. No. 3,567,763 and in DE Patent No. 1,231,688; reaction products of the aforementioned isocyanates with acetylene according to DE Patent No. 1,072,385: and polymeric fatty acid ester-containing polyisocyanates according to U.S. Pat. No. 3,455,883.

Technically easily accessible polyisocyanates are, as a rule, particularly preferred, for example the 2,4- and 2,6-toluylene-diisocyanates as well as desired mixtures of these isomers ("TDI"), polyphenyl-polymethylene-polyisocyanates as produced by anilineformaldehyde-condensation and subsequent phosgenation ("crude MDI") and polyisocyanates having carbodiimide groups, urethane groups, allophanate groups, isocyanurate groups or biuret groups ("modified polyisocyanates"), in particular such modified polyisocyanates, which derive from 2,4- and/or 2,6-toluylene-diisocyanate or 4,4'- and/or 2,4'- and/or 2,2'-diphenylmethane-diisocyanate. Toluylene-2,4-diisocyanate is particularly preferred.

The polyisocyanate can also be used in the form of a (concentrated) solution in a solvent which is inert in relation to isocyanates and which is immiscible with water, preferably aliphatic and aromatic hydrocarbons such as n-hexane, cyclohexane, isooctane, benzene, toluene, xylene or similar substances; however, this is not preferable.

It was surprising and unforeseeable for those skilled in the art that in spite of a chemical reaction, during which substantial quantities of gas are generated, the production of small particles with approximately spherical appearance is possible.

When carrying out the invention, a solution of water, a suitable protective colloid and optionally an emulsifier are initially produced for example with simple stirring. These two or three components form the aqueous phase of the process.

Non-ionic, anionic or cationic surface-active agents of HLB (hydrophilic-lipophobic-balance) range from about 10 to 18, preferably from about 13 to 16, can be used as emulsifiers in the aqueous or continuous phase. The HLB-value is described in a publication by Atlas-Chemie, 4300 Essen, from the year 1968. It gives numerous surface-active agents that fall in this range, for example compounds such as sodium-propyl- naphthalene-sulphonate, polyoxyethylene-sorbitoleatelaurate, ethoxylated nonylphenols, polyethylene-glycol ethers of linear alcohols or polyethylene-glycol esters of linear carboxylic acids. The surface-active agents are preferably added, as described, to the aqueous phase, but may also be added to the organic phase. Without particular indications regarding the phase in which the surface-active agent is to be added, a distribution of this agent between the phases according to phase mixing, takes place according to the relative solubility. The use of a surface-active agent can also be excluded when during the formation of the dispersion, sufficiently high shearing rates are applied or the protective colloid also has a sufficient effect as an emulsifier. According to a preferred embodiment of the invention, surface-active emulsifiers are used. The concentration of this agent in the system is most favorably about 0.001 to 3.0% by weight, based on the aqueous phase. Relatively high concentrations can be used, without increasing the dispersibility.

A critical component of the aqueous or continuous phase to be used according to the invention is a protective colloid which can be selected from a multitude of such materials. Examples of suitable protective colloids are: polyacrylates, methyl cellulose, polyvinyl alcohols, polyacrylamides and poly(methyl vinyl ethers/maleic acid anhydrides). Protective colloids based on polyvinyl alcohol and methyl cellulose are preferred. The quantity of protective colloid is dependent on various factors such as molecular weight, type and effectiveness within the media, compatibility and similar properties. The protective colloid should be added to the aqueous phase before addition of the organic polyisocyanate. It is less preferable to add the protective colloid to the system subsequent to the addition of the organic polyisocyanate or after dispersion. Furthermore, part of the protective colloid can be added before addition of the organic polyisocyanate and a further part after dispersion. The protective colloid is used in an amount of about 0.01 to 5.0% by weight, preferably about 0.01 to 0.5%.by weight, based on the aqueous phase.

The quantity of organic polyisocyanate, based on the total reaction mixture, can be from about 1 to 65% by weight. The preferred quantity of organic polyisocyanate is about 10 to 30% by weight, most preferably about 15 to 25% by weight.

To form the dispersion, the organic polyisocyanate is added to the aqueous phase, optionally with stirring. Suitable dispersing agents may be used for dispersing one liquid in another. Supersonic crushing devices are used or devices wherein streams of material through nozzles are hurled with a high velocity against each other or against impact devices. Particularly suitable, however, are such devices where the dispersion to be crushed is hurled with a high velocity and shearing effect through grids or slits. This is achieved by machines operating according to the rotor-stator principle. The materials are pressed through apertured plates superimposed on each other and running in opposite directions to each other; through rotating cylinders with slits, between which there is only a narrow gap; or through toothed rings rotating in opposite directions. Such devices are known and are described, for example, as mixing sirens. Devices which operate according to the rotor-stator principle are preferably used and include those offered commercially under the names Supraton, Condix Mischer, or Ultraturrax. Such particularly well suited mixing aggregates allow the thorough mixing of liquid materials with an output in the mixing head region of about 15 to 250 watts/cm$^3$.

As soon as the desired droplet size is achieved, the intensive mechanical dispersing (preferably at from +10 to +40° C., particularly at room temperature) is discontinued. This droplet size is about 0.5 to 200 μm, particularly about 0.5 to 20 μm, and determines the particle size of the desired, solid urea group-containing polyisocyanates. During the second phase of the process, only moderate movement is required.

After production of the finely-divided dispersion, the reaction between the organic polyisocyanate and water takes place at about 10° to 80° C., preferably about 20° to 40° C. The reaction is preferably conducted under normal pressure. However, the operation can also take place with the utilization of suitable devices under increased pressure (which can build itself up through the released $CO_2$) or under reduced pressure.

The resulting urea group-containing polyisocyanates are sparingly soluble in water and thus generally escape a further reaction of the NCO-groups still present with the water, so that generally, of the organic polyisocyanates used, only one NCO-group per molecule participates in the formation of urea groups. The NCO-contents of the products obtained according to the process of the invention, are in most cases only slightly under the calculated NCO-content. However, products with a substantially reduced NCO-content in relation to theory, i.e. wherein an oligourea formation has taken place, are also of interest for certain uses.

At relatively high reaction temperatures, the solubility of the urea group-containing polyisocyanate increases, so that a further reaction with water resulting in the formation of polymeric or oligomeric ureas can take place. The reaction temperature should thus generally be maintained under 40° C. The quantity of protective colloids or dispersing auxiliaries must also be kept within the given quantity limits, so as not to make it too strongly hydrophilic and thus consequently trigger a further reaction of the NCO-groups in the formed urea diisocyanate.

So as to accelerate the reaction between water and the organic polyisocyanate, catalysts commonly used in polyurethane chemistry, such as tertiary amines (N,N-dimethylbenzylamine, triethylamine, pyridine, bis(-dimethyl aminoethyl)ethers) or organometallic compounds (tributyl-tin-acetate, di-n-butyl-tin-diacetate, Sn(II)dioctoate, dibutyl-tin-dilaurate) are preferably used in catalytically effective quantities. The addition of catalysts takes place preferably after the formation of an emulsion. The catalyst quantity which is normally within the range of 0,01–10 , preferably 0,1–4 % by weight, based on polyisocyanate, is preferably selected, such that the reaction is finished after about 2 to 8 hours, and the generated heat of reaction does not heat the mixture to more than 35° C., so that an external cooling is unnecessary.

The reaction between the organic polyisocyanate and water is to be observed during the generation of $CO_2$. This can lead, particularly with relatively high emulsifier and protective colloid concentrations, to substantial foam formation and/or volume expansion, which disturb the working-up of the reaction mixture. One possibility is offered by the chemical binding of $CO_2$ by carrying out the reaction at a pH$\geq$7 to about 10 (preferably about 8.5 to 9.5), the pH being maintained in the aforementioned range by addition of bases, for example an aqueous sodium hydroxide solution. A commercial anti-foaming agent, for example, tributyl phosphate can additionally or alternatively be added.

When the reaction has ended (this being observed when the generation of $CO_2$ ceases) the solids suspension is drawn off by suction via a suitable filter, washed with water, and then optionally again washed with a solvent, for example ethyl acetate or acetone, which is inert with regard to isocyanates and optionally has a certain water-solubility, and is dried in a drying chamber, preferably in a vacuum, at a low temperature (50° C.).

If tertiary amines are used as catalysts, they can be completely converted in the aqueous phase by addition of an equivalent acid quantity in the form of salts thereof, so that they are no longer present in the solid polyisocyanate after the working-up thereof. Other known processes for the removal of catalysts are possible. The conversion reaction can optionally be ended by deactivating the catalyst at a point in time before the actual end of the reaction.

In applying the process according to the invention, products with an almost perfect spherical form are obtained. The particle diameters are generally from about 1 to 20 μm.

The invention is further illustrated, but is not intended to be limited by the following examples in which all parts and percentages are by weight unless otherwise specified.

EXAMPLES

Starting compounds used protective colloid 1: polyvinyl alcohol Mowiol ® 26/88 made by Hoechst Frankfurt/Main protective colloid 2: methyl cellulose (cellulose methyl ethers) Tylose ®MH 50 made by Hoechst Frankfurt/Main emulsifier 1: Atlox ® 4851 B made by Atlas Chemie, Essen. A mixture of anionic and non-ionic surfactants, HLB-value 13.2 emulsifier 2: commercial adduct of 10 mol of ethylene oxide and 1 mol of nonylphenol (HLB 13.9).

GENERAL DESCRIPTION OF THE EXPERIMENTAL METHOD FOR THE PRODUCTION OF UREA DIISOCYANATES

The given quantity of water (preferably demineralized water) was homogeneously mixed at room temperature in a 2 l glass beaker with the given quantity of protective colloid (preferably in the form of an about 10% aqueous solution), and the given quantity of emulsifier (preferably in the form of 1% solution).

The weighed quantity of the starting polyisocyanate was then added and the two-phase mixture was then intensively mixed with an Ultraturrax-stirrer (type T 45/N made by IKA-Werk, Staufen i. Breisgau), (speed regulator set to from about ⅓ to ½ of the full capacity) until a stable emulsion is obtained (generally 3 mins). This was transferred into a 2 l sulphonating beaker with a surface grinding lid and further stirred with a standard blade stirrer.

After addition of the given catalyst, the generation of $CO_2$ which took place during the reaction was traced with a gas meter. When the generation of $CO_2$ had finished, neutralization was carried out with the given quantity of 1 N HCl, the suspension was drawn off by suction after stirring for about 10 min, the filter residue was washed several times with water and dried at 50° C. in the vacuum drying chamber.

EXAMPLE 1

(see general description of the experimental method)

| aqueous phase: | 500 g of water |
| --- | --- |
| | 0.05 g of emulsifier 1 |
| | 0.25 g of protective colloid 1 |
| polyisocyanate: | 150 g of 2,4-toluylene diisocyanate |
| catalyst: | 1 g of pyridine |
| neutralization: | 13 ml of 1 N HCl |

134.3 g (96.8%) of a finely divided product were obtained with an NCO content of 23.02% by weight and a particle size of ≦20 μm.

DETERMINATION OF THE NCO CONTENT IN TH EUREA DIISOCYANATES

A weighed quantity of from about 1 to 2 g of the polyisocyanate to be titrated was added to 20 ml of 1 N-dibutylamine solution in chlorobenzene and heated for about 2 min to about 80° C. with occasional agitation. 30 ml of dimethylformamide were then added and the excess of dibutylamine was back-titrated with 1 N HCl.

EXAMPLE 2

| aqueous phase: | 500 g of water |
| --- | --- |
| | 0.5 g of protective colloid 1 |
| polyisocyanate: | 150 g of 2,4-toluylene diisocyanate |
| catalyst: | 2.0 g of pyridine |
| neutralization: | 26.0 ml of 1 N HCl |

132.6 g (95.5%) of a pulverulent product with an NCO-content of 22.43% by weight were obtained, which consisted for the most part of spherical shaped particles with a diameter of 3 to 7 μm.

EXAMPLE 3

(Comparative example—without protective colloid)

| aqueous phase: | 500 g of water |
| --- | --- |
| | 0.1 g of emulsifier 2 |
| polyisocyanate: | 150 g of 2,4-toluylene diisocyanate |
| catalyst: | 2.0 g of pyridine |
| neutralization: | 26.0 ml of 1 N HCl |

During the reaction, the resulting urea group-containing polyisocyanate was deposited in the form of a very solid cake on the inside wall of the reaction vessel. This can be removed, for example, by pouring off the aqueous phase and cooling the flask and the contents thereof to −60° C. and yielded 120.1 g (86.5%) of a product with an NCO content of 22.80% by weight after drying and crushing in a mortar. The crushed particles have no spheroidal appearance.

EXAMPLE 4

(Comparative example accoding to Example in U.S. Pat. No. 3,906,019 in column 3, lines 1–16)

300 g of 2,4-toluylene diisocyanate,
100 g of water and
7 g of pyridine were intensively mixed with each other by stirring in a 2 l surface grinding reaction vessel with a surface grinding lid. Only with intensive ice sodium chloride cooling, can the reaction temperature be maintained at not more than 42° C. The reaction was terminated after about 1 h. When the reaction had ended, the remaining water was poured off and the product firmly clinging to the inside wall of the reaction vessel was removed by means of a spatula, drawn off by suction and elutriated 2 times in hexane, drawn off by suction and dried.

Yield: 238.3 g=85.8% in the form of very coarse, up to 2 cm thick chunks.

NCO content: 21.66% by weight.

EXAMPLE 5

(Comparative example according to Example 1 in U.S. Pat. No. 3,906,019)

325 g 2,4-toluylene diisocyanate,
50 g water and
1.75 g of pyridine were intensively mixed in an open glass beaker. The temperature of the reaction mixture was maintained at 30° to 40° C. through addition of about 50 g of ice. The reaction was terminated after about 30 min.

The product was drawn off by suction, washed 2 times with hexane and dried at 50° C. in a vacuum drying chamber.

Yield: 210.5 g=70% in the form of very coarse, up to 1 cm thick chunks.

NCO content: 24.5% by weight.

The product had an intense pyridine odor.

EXAMPLE 6

| aqueous phase: | 500 g of water |
| | 0.75 g of protective colloid 1 |
| | 0.15 g of emulsifier 2 |
| polyisocyanate: | 150 g of 2,4'-toluylene diisocyanate |
| catalyst: | 2.0 g of pyridine |
| neutralization: | 26.0 ml of 1 N HCl |

111.68 g (80.5%) of a very finely-divided, agglomerate-free powder with an NCO content of 19.40% by weight was obtained which consisted of ideal round spheres with a diameter of ≦15 μm. There were losses during filtration due to portions of extremely finely-divided solids, which are not retained by the filter.

EXAMPLE 7

| aqueous phase: | 500 g of water |
| | 0.25 g of protective colloid 2 |
| | 0.05 g of emulsifier 1 |
| polyisocyanate: | 150 g of 2,4-toluylene diisocyanate |
| catalyst: | 0.5 g of pyridine |
| neutralization: | 6.5 ml of 1 N HCl |

134.3 g (96.8%) of a finely-divided product with an NCO content of 22.90% by weight and an average particle size of about 10 μm was obtained.

EXAMPLE 8

| aqueous phase: | 500 g of water |
| | 0.05 g of emulsifier 1 |
| | 0.25 g of protective colloid 1 |
| polyisocyanate: | 150 g of 2,4-toluylene diisocyanate |
| catalyst: | in each case 2 g of a compound mentioned below |
| neutralization: | in each case with the given quantity of 1 N HCl |

The resulting products were fine powders with a particle size of about 15 μm.

| Experimental catalyst | ml 1 N HCl | Yield g | Yield % | % NCO of the product |
|---|---|---|---|---|
| A triethylamine | 20.69 | 133.0 | 95.8 | 21.81 |
| B triethylene diamine | 22.89 | 133.4 | 96.1 | 22.30 |
| C dimethylbenzylamine | 15.02 | 132.3 | 95.2 | 22.50 |
| D pyridine | 26.00 | 129.02 | 93.0 | 22.60 |
| E N—methylmorpholine | 20.58 | 132.5 | 95.5 | 24.0 |
| F bis(dimethylaminoethylether) | 17.43 | 135.4 | 97.6 | 21.95 |
| G tetremethyl urea | 0.10 | 134.7 | 97.1 | 24.30 |
| H UL 1 made by Witco dibutyl-Sn—dimencaptide | 0.20 | 134.6 | 97.0 | 23.93 |
| I Sn(II) octoate | 0.00 | 132.2 | 95.2 | 23.90 |

| | A | B | C | |
|---|---|---|---|---|
| aqueous phase | 500 g | 700 g | 1000 g | of water |
| | 0.25 g | 0.25 g | 0.25 g | of protective colloid 1 |
| | 0.05 g | 0.05 g | 0.05 g | of emulsifier 1 |
| polyisocyanate | 150 g | 150 g | 150 g | of 2,4-toluylene diisocyanate |
| catalyst | 1.0 g | 1.0 g | 1.0 g | of pyridine |
| neutralization | 13.0 ml | 13.0 ml | 13.0 ml | of 1 N HCl |
| yield | 134.3 g (96.8%) | 134.9 g (97.2%) | 133.6 g (96.3%) | |
| NCO content | 23.02 | 24.0 | 23.19 | % by weight |
| particle size | ≦20 μm | ≦10 μm | ≦10 μm | |

EXAMPLE 10

| aqueous phase: | 500 g of water |
| | 0.25 g of protective colloid 1 |
| | 0.05 g of emulsifier 1 |
| polyisocyanate: | 150 g of a crude polyisocyanate resulting from the phosgenation of aniline-formaldehyde condensation products and having an NCO content of 31% by weight, viscosity ≦100 mPas at 25° C. |
| catalyst: | 2.0 g of pyridine |
| neutralization: | 26.0 ml of 1 N HCl |

130.6 g (about 91.8%) of a very finely-divided agglomerate-free powder with an NCO content of 8.48% by weight and a particle size of from 6 to 26 μm was obtained which was present entirely in the form of ideal round spheres.

EXAMPLE 11

| aqueous phase: | 500 g of water |
| | 0.25 g of protective colloid 1 |
| | 0.05 g of emulsifier 1 |
| polyisocyanate: | 120 g of a mixture of about 35% by weight of 4,4'-diisocyanatodiphenylmethane and about 65% by weight of 2,4'-diisocyanatodiphenylmethane |
| catalyst: | 1.0 g of pyridine |
| neutralization: | 26.0 ml of 1 N HCl |

131.6 (about 92.5%), of a very finely-divided powder containing only a very small amount of agglomerates with an NCO content of 5.80% by weight and a particle size of from 5 to 20 μm was obtained which was present entirely in the form of ideal round spheres.

EXAMPLE 12

| aqueous phase: | 500 g of water |
| --- | --- |
| | 0.75 g of protective colloid 1 |
| | 0.1 g of emulsifier 1 |
| polyisocyanate: | 150 g of isophoronediisocyanate |
| catalyst: | 1.0 g of UL 1 (see Example 8) |
| neutralization: | 0.2 ml of 1 N HCl |

72.4 g (51.3%) (losses during working-up) of a product with an NCO content of 10.10% by weight and a particle size of up to about 200 μm was obtained, the largest part of which was present in the form of spheres with a diameter of ≦80 μm.

| aqueous phase: | 500 g of water |
| --- | --- |
| | 0.05 g of emulsifier 1 |
| | 0.25 g of protective colloid 1 |
| | 0.09 g of tributylphosphate as an anti-foaming agent |
| polyisocyanate: | 150 g of 2,4-toluylene diisocyanate |
| catalyst: | 1.0 g of pyridine |
| neutralization: | 13 ml of 1 N HCl |

131.3 g (94.60%) of a product with an NCO content of 24.0% by weight and a particle size of ≦13 μm was obtained which exhibited only very slightly agglomerated particles. A clearly reduced increase, in relation to Example 1, of the foam resulting from the development of $CO_2$ was observed.

EXAMPLE 14

Production of an elastomer from a relatively high molecular weight polyether diamine with aromatic amino groups and the urea group-containing polyisocyanate according to Example 1.

Production of the relatively high molecular weight aromatic polyamine (starting material)

1 mol of a linear polypropylene ether glycol with an OH-number of 56 and 2 mol of toluylene-2,4-diisocyanate was converted to an NCO-prepolymer (3.58% NCO) after heating for 4 hours at 80° C. 810 g of the heated NCO-prepolymer at 45° C. were then added under intensive stirring to a cooled solution of 52.2 g of potassium hydroxide and 500 ml of water and 300 ml of acetone (NCO:OH ratio=1:1.35) such that an internal temperature of 25° C. was not exceeded. Further stirring was carried out at this temperature for 30 mins and then it was heated for 2 h to reflux. After standing for 30 mins the lower aqueous salt solution was separated from the two-phase reaction mixture and disposed of. The upper phase at 20 mbar/80° C. and then at 1 mbar/100° C. was freed from water residues and acetone residues. By drawing off the product heated to 60° C. by suction via a pressure suction filter (3 bars excess pressure), small salt residues were separated and the polyetheramine with are NH-number of 48.4 was isolated.

Production of the elastomer 100 parts of the relatively high molecular weight aromatic polyamine were intensively mixed with 20 parts of the finely-divided polyisocyanate in Example 1, immediately degassed in a water jet vacuum, poured into a large, open, cold mold, about 20 cm×20 cm×0.5 cm and thoroughly heated in a heating chamber for 4 hours at 120° C. Table 1 shows the mechanical values of the elastomers obtained. The degassed mixture of aromatic amino-polyether and polyisocyanate during slow heating (about 10 K/min), at about 88° C. shows a sudden and substantial increase in viscosity with the development of a plastic to an elastic phase.

TABLE 1

| Resistance to tensile stress | DIN 53 504 | 11.3 MPa |
| --- | --- | --- |
| elongation at tear | DIN 53 504 | 200% |
| further ultimate tensile strength | DIN 53 515 | 35.7 kN/m |
| shore hardness | DIN 53 505 | 92 A |
| | | 42 D |
| elasticity | DIN 53 512 | 51% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the productin of urea group-containing, finely divided solid polyisocyanates which comprises emulsifying or suspending a urea group-free organic polyisocyanate in an excess of water so that said organic polyisocyanate amounts to about 1 to 65% by weight of the reaction mixture, said water containing about 0.01 to 5% by weight, based on the aqueous phase, of a protective colloid, reacting the organic polyisocyanate with water to yield a urea group-containing polyisocyanate and separting and recovering said urea group-containing, finely divided solid polyisocyanates.

2. The process of claim 1 wherein the reaction of said organic polyisocyanate with water is conducted in the presence of a catalyst while maintaining a pH of 7 to 10, optionally with the addition of a base.

3. The process of claim 1 wherein said protective colloid comprises a member selected from the group consisting of polyvinyl alcohols, methyl cellulose, polyacrylates, polyacrylamides and polymethylvinylether/maleic acid anhydride copolymers.

4. The process of claim 1 wherein said protective colloid comprises a member selected from the group consisting of polyvinyl alcohols and methyl cellulose.

5. The process of claim 1 wherein the reaction is conducted in the presence of a nonionic, anionic and/or cationic surface-active agent having an HLB value of about 10 to 18, said surface-active agents being present in a quantity of about 0.001 to 3% by weight, based on the aqueous phase.

6. The process of claim 1 wherein said organic polyisocyanate is present in an amount of about 10 to 30% by weight, based on the total reaction mixture.

7. The process of claim 1 wherein said organic polyisocyanate is 2,4-toluylene diisocyanate.

8. The process of claim 1 wherein the emulsifying or suspending step comprises mechanically intensively dispersing the polyisocyanate in the aqueous medium comprising water and the protective colloid to produce droplets with a particle size of about 0.5 to 20 μm and reacting said organic polyisocyanate with water at a temperature of about 20° to 40° C.

9. The process of claim 2 which comprises deactivating or removing the catalyst before separating the solid urea diisocyanate.

* * * * *